United States Patent [19]

Smith

[11] Patent Number: 4,867,887

[45] Date of Patent: * Sep. 19, 1989

[54] METHOD AND APPARATUS FOR SEPARATING MONONUCLEAR CELLS FROM BLOOD

[75] Inventor: Ward C. Smith, Mahwah, N.J.

[73] Assignee: Becton Dickinson and Company, Franklin Lakes, N.J.

[ * ] Notice: The portion of the term of this patent subsequent to Jul. 4, 2006 has been disclaimed.

[21] Appl. No.: 217,947

[22] Filed: Jul. 12, 1988

[51] Int. Cl.$^4$ ............................................. B01D 21/26
[52] U.S. Cl. ..................................... 210/782; 210/516; 210/789; 422/101; 436/177; 494/37
[58] Field of Search ...................... 494/16–20, 494/37; 210/782, 789, 516, 518, 514; 435/2; 422/101, 102; 436/177

[56] References Cited

U.S. PATENT DOCUMENTS

| | | | |
|---|---|---|---|
| 3,852,194 | 12/1974 | Zine, Jr. | 210/789 |
| 3,920,549 | 11/1975 | Gigliello et al. | 210/516 |
| 3,945,928 | 3/1976 | Ayres | 210/516 |
| 3,960,727 | 6/1976 | Hochstrasser | 210/782 |
| 4,101,422 | 7/1978 | Lamont et al. | 210/516 |
| 4,147,628 | 4/1979 | Bennett et al. | 210/516 |
| 4,153,739 | 5/1979 | Kessler | 427/2 |
| 4,190,535 | 2/1980 | Luderer et al. | 210/789 |
| 4,255,256 | 3/1981 | Ferrante et al. | 210/789 |
| 4,310,430 | 1/1982 | Ichikawa et al. | 210/782 |
| 4,350,593 | 9/1982 | Kessler | 210/516 |
| 4,417,981 | 11/1983 | Nugent | 210/516 |
| 4,435,293 | 3/1984 | Graham, Jr. et al. | 210/782 |
| 4,436,631 | 3/1984 | Graham, Jr. et al. | 210/518 |
| 4,457,782 | 7/1984 | Honda et al. | 210/516 |
| 4,487,700 | 12/1984 | Kanter | 210/789 |
| 4,534,798 | 8/1985 | Honda et al. | 210/510.1 |
| 4,640,785 | 2/1987 | Carroll et al. | 210/782 |
| 4,751,001 | 6/1988 | Saunders | 210/516 |
| 4,816,168 | 3/1989 | Carrol et al. | 210/516 |
| 4,818,418 | 4/1989 | Sauders | 210/782 |

FOREIGN PATENT DOCUMENTS 1127537 7/1982 Canada .
0036168 9/1981 European Pat. Off. .

OTHER PUBLICATIONS

Iodinated Density Gradient Media, by Dr. D. Rickwood, Chapter 7, by IRL Press, (1983).
Rapid, Quantitative Human Lymphocyte Separation and Purification in a Closed System, by Luderer et al., Molecular Immunology, 16, pp. 621–624, (1979).
Comparison of T and B Cell Analyses on Fresh and Aged Blood, by J. K. A. Nicholson et al., Journal of Immunological Methods, 73, pp. 29–40, (1984).
Experimental Cell Research, by Splinter et al., (1978), pp. 245–251.
9265X, Chemical Abstract.

Primary Examiner—W. Gary Jones
Attorney, Agent, or Firm—Hoffmann & Baron

[57] ABSTRACT

A blood separation device includes a collection tube containing a first layer of a thixotropic gel-like substance and a second layer of a newtonian gel-like substance which is positioned below the first layer. The first layer of the thixotropic substance is positioned between the second layer of the newtonian substance and a blood sample received by the tube, prior to centrifuging the tube, and acts as a barrier between the second layer and the blood sample to prevent intermixing of the second layer and the blood sample. The thixotropic gel-like substance of the first layer has a specific gravity which is greater than the newtonian gel-like substance of the second layer whereupon centrifugation of the tube, the first layer moves to a position below the second layer. The second layer of the newtonian gel-like substance acts as a density separation medium, the newtonian gel-like substance being formed with a specific gravity such that the second layer is adapted to assume a position in the collection tube, upon centrifugation of the tube, between the mononuclear cells and the heavier components of the blood sample placed in the tube.

30 Claims, 2 Drawing Sheets

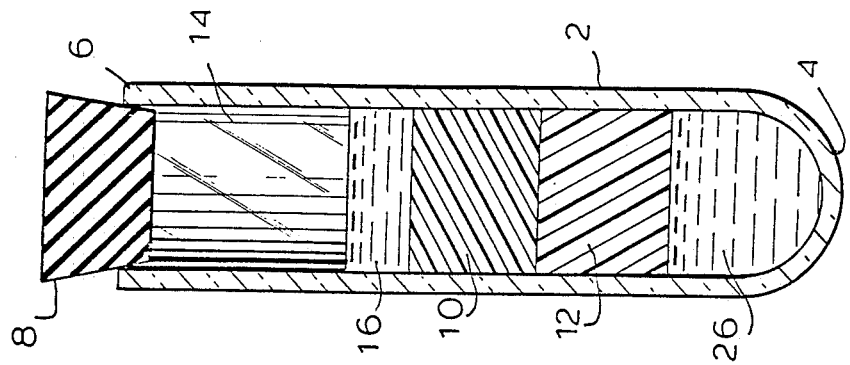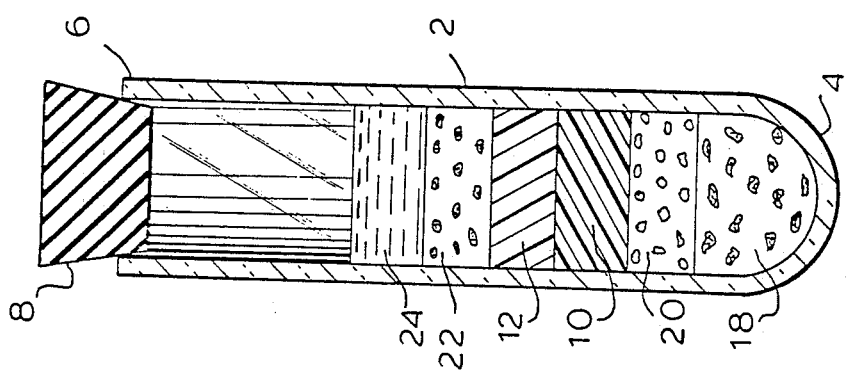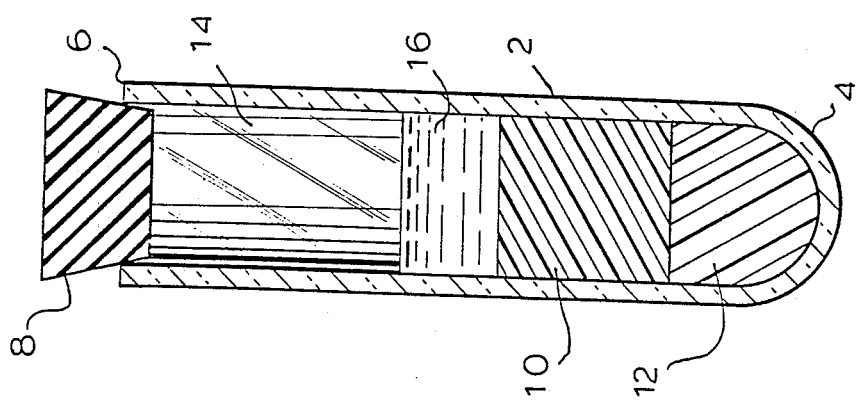

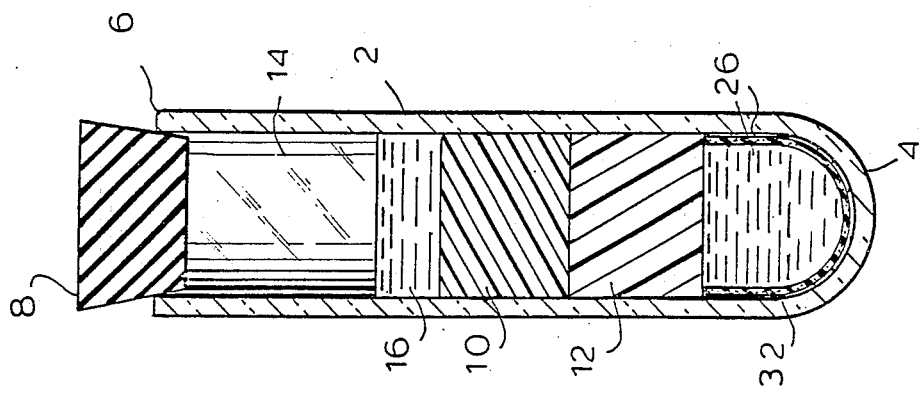
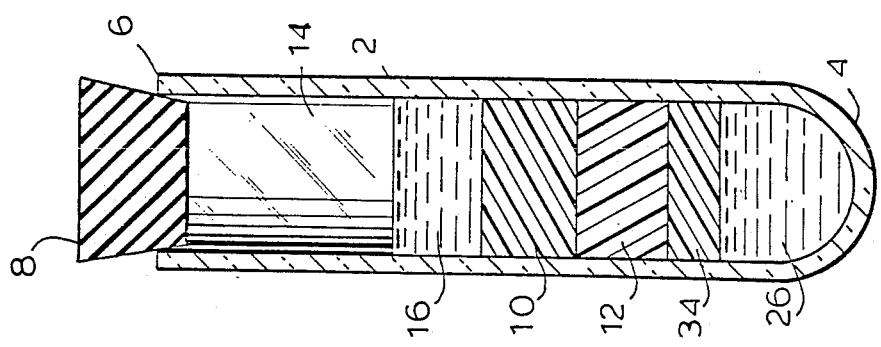
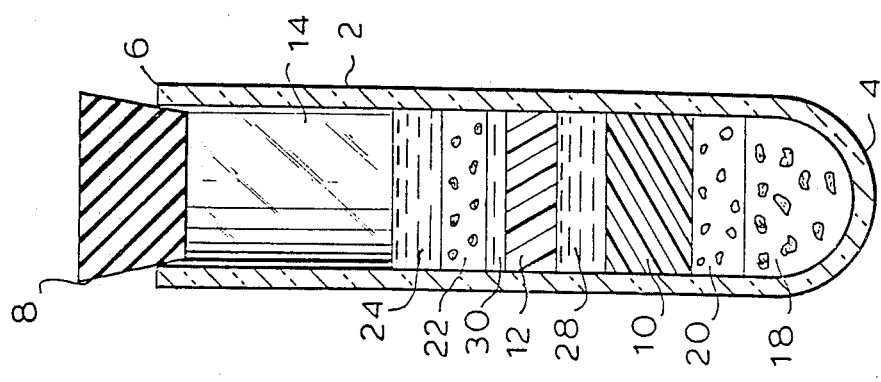

METHOD AND APPARATUS FOR SEPARATING MONONUCLEAR CELLS FROM BLOOD

BACKGROUND OF THE INVENTION

1. Field of the Invention

This invention relates to the separation of mononuclear cells from whole or diluted blood, and more particularly relates to a blood separation device and a method of separating blood components using such a device.

2. Description of the Prior Art

A well known blood separation device on the market today includes a blood collection tube containing an aliquot of a newtonian gel and an aliquot of a liquid density medium, such as Ficoll-Paque (TM). The newtonian gel acts as a barrier between the liquid density medium and a sample of blood placed in the tube atop the gel. When the tube is centrifuged, the liquid density medium acts to separate the mononuclear cells from the other blood components.

The conventional blood separation device described above works well for clinical laboratory applications, where a blood sample is placed in the tube and immediately centrifuged to separate out the targeted blood components. The device is not intended for use as, nor can it function as, a shippable blood separation device, i.e., such as where the physician draws a blood sample into the collection tube and sends it to a laboratory for centrifugation or further processing.

The reason why such devices cannot be shipped is that both the gel and the density medium are liquids and will not retain their pre-processed positions in the tube. Although each is immiscible with respect to the other, they will run in the tube when the tube is placed on its side. Accordingly, when the device is in such a position or if the device is disturbed, the newtonian gel may no longer be in position between the liquid density medium and a blood sample contained in the tube, and thus may no longer act as a barrier between the two. The blood sample will mix with the liquid density medium and affect its blood separation characteristics, namely its specific gravity or density, and consequently its ability to properly separate the mononuclear cells from the other components of the blood sample.

OBJECTS AND SUMMARY OF THE INVENTION

It is an object of the present invention to provide a blood separation device which is shippable.

It is another object of the present invention to provide a method for separating the mononuclear cells from the other components of a blood sample.

It is a further object of the present invention to provide a blood separation device and method for using the same which overcomes the inherent disadvantages of known separation devices, such as that described previously.

In accordance with one form of the present invention, a blood separation device, and in particular one which is adapted for separating mononuclear cells from whole or diluted blood, includes a collection tube having a bottom end which is closed and an opposite top end which is open for receiving a blood sample. The collection tube is adapted to be centrifuged.

The device further includes a first layer of a thixotropic gel-like substance contained in the collection tube, and a second layer of a newtonian gel-like substance, also contained in the collection tube and positioned below the first layer.

The collection tube is formed to be of a sufficient size to define a free space above the first layer of the thixotropic substance to receive the blood sample.

The first layer of the thixotropic substance is positioned between the second layer of the newtonian substance and a blood sample received by the tube, prior to centrifuging the tube, and acts as a barrier between the second layer of the newtonian substance and the blood sample to prevent the intermixing or intermingling of the second layer and the blood sample. Accordingly, the thixotropic gel will not run and will maintain the separation of the blood sample and the newtonian gel even when the tube is placed on its side, as during shipment from physician to laboratory.

The thixotropic gel-like substance of the first layer has a specific gravity which is greater than that of the newtonian gel-like substance of the second layer. Upon centrifugation of the tube, the first layer moves to a position below the second layer of the newtonian substance.

The second layer of the newtonian gel-like substance acts as a density separation medium. The newtonian gel-like substance is formed with a specific gravity so that the second layer is adapted to assume a position in the collection tube, upon centrifugation of the tube, between the mononuclear cells and the heavier components of the blood sample placed in the tube.

In accordance with another form of the invention, a blood separation device includes a collection tube, such as in the form described above, having at its closed end a liquid density gradient medium, followed in order by a newtonian gel, a thixotropic gel, and a stabilizing reagent for in vitro storage of the blood sample in the collection tube.

These and other objects, features and advantages of this invention will become apparent from the following detailed description of illustrative embodiments thereof, which is to be read in connection with the accompanying drawings.

BRIEF DESCRIPTION OF THE DRAWINGS

FIG. 1 depicts a blood separation device formed in accordance with one form of the present invention.

FIG. 2 shows the state of the blood components and other elements of the blood separation device illustrated by FIG. 1 after the device containing a sample of blood is centrifuged.

FIG. 3 illustrates a blood separation device of the present invention, formed in accordance with a second embodiment and prior to centrifugation, the device containing a a stabilizing reagent or other solution.

FIG. 4 depicts the state of the blood components and other elements of the blood separation device illustrated by FIG. 2 after the device containing a sample of blood is centrifuged.

FIG. 5 depicts a blood separation device formed in accordance with a third form of the present invention.

FIG. 6 depicts a blood separation device formed in accordance with a fourth form of the present invention.

DETAILED DESCRIPTION OF THE PREFERRED EMBODIMENTS

Referring initially to FIG. 1 of the drawings, it will be seen that a blood separation device constructed in accordance with one form of the present invention includes a collection tube 2, which may be in the form of a test tube, having a closed bottom end 4 and an opposite open top end 6. The open top end 6 may be fitted with a removable stopper or other closure 8, which closure is pierceable with a needle so that a blood sample may be added to the collection tube 2. Additionally, the collection tube 2 may be evacuated to all blood to be drawn from the patient directly into the tube.

The blood separation device of the present invention, in the form illustrated by FIG. 1, employs a first layer 10 of a thixotropic gel-like substance contained in the tube, and a second layer 12 of a newtonian gel-like substance, also contained in the collection tube and positioned below the first layer 10.

The collection tube 2 is of sufficient size to define a free space 14 above the first layer 10 of thixotropic gel. This space is, of course, provided to receive a sample of whole or diluted blood.

The first layer 10 of the thixotropic gel-like substance is positioned between the second layer 12 of the newtonian gel and a blood sample (not shown) received by the tube, prior to centrifuging the tube. The first layer 10 acts as a barrier between the second layer 12 of the newtonian gel and the blood sample to prevent the second layer 12 from intermixing with the blood sample.

As described previously, the conventional blood separation device which includes a newtonian gel, when placed on its side, caused the newtonian gel to "slump", that is, run in the longitudinal direction of the tube. In the present invention illustrated by FIG. 1, the newtonian gel layer 12 is held in position at the closed end 4 of the collection tube by the thixotropic gel layer 10, and is maintained in an unmixed state with the blood sample.

In the blood separation device illustrated by FIG. 1, the thixotropic gel-like substance of the first layer 10 has a specific gravity which is greater than that of the newtonian gel-like substance of the second layer 12 so that, upon centrifugation of the tube, the first layer 10 moves to a position below the second layer 12. This is illustrated by FIG. 2 of the drawings.

The second layer 12 of the newtonian gel-like substance acts as a density separation medium. The newtonian gel is formed with a specific gravity such that the second layer 12 is adapted to assume a position in the collection tube 2, upon centrifugation of the tube, between the mononuclear cells and the heavier components of the blood sample placed in the tube.

As illustrated by FIG. 1 of the drawings, the blood separation device may also include a solution 16 such as an anti-coagulant, a stabilizing reagent, or a combination of the two, which solution is mixed with the blood sample to maintain the viability of the blood cells after the sample is drawn by the physician and during shipment to a clinical laboratory for further processing or centrifugation.

Upon centrifugation, the blood components and the thixotropic and newtonian gel-like substances of the first and second layers, respectively, assume the positions shown in FIG. 2. The red blood cells, or erythrocytes 18, which are generally the heaviest blood components, gravitate toward the bottom closed end 4 of the collection tube. The first layer 10 of the thixotropic gel, which has a specific gravity greater than that of the newtonian gel of the second layer 12, moves to a position beneath the second layer 12 of the newtonian gel. Granulocytes 20 of the blood sample are generally disposed between the thixotropic gel layer 10 and the red blood cells 18.

The newtonain gel layer 12 now forms the upper barrier in the collection tube 2, with the mononuclear cells 22 generally disposed above the surface of the newtonian gel layer. The newtonian gel-like substance, which is used as the density separating medium, is formed with a particular specific gravity that is intermediate the specific gravities of the phases of the blood to be separated. FIG. 2 shows the layer 12 of newtonian gel as forming a barrier between the heavier components of the blood, such as the granulocytes 20 and the red blood cells 18, and the plasma 24 of the blood and the mononuclear cell fraction 22 containing the platelets, lymphocytes and monocytes.

The plasma 24 of the blood may be removed, care being exercised to avoid disturbing the mononuclear cell fraction 22 containing platelets, lymphocytes and monocytes. This operation may be carried out by means of a pipette (not shown), leaving the platelets, lymphocytes and monocytes atop the newtonian gel-like barrier layer 12. Thereafter, a diluent, such as an isotonic $Ca+2$, $Mg+2$ -free salt buffer solution, is gently run into the collection tube 2 onto the newtonian gel layer 12. The tube may then be gently rocked or otherwise agitated to cause the platelets, lymphocytes and monocytes which had been resting on the newtonian gel layer 12 to be suspended in the buffer solution, and this suspension may then be removed from the tube 2 by using a pipette (not shown) for further processing according to standard and well known procedures.

One of the advantages of the blood separation device illustrated by FIG. 1 and described above is that the layer 12 of the newtonian gel-like substance, which supports the mononuclear cells 22 in the collection tube after separation, helps minimize the red cell contamination which is experienced by blood separation devices using a thixotropic gel as the separation medium, such as described in U.S. Pat. No. 4,190,535 to Luderer, et al. Because of the lower viscosity of the newtonian gels, the gel layer 12 presents a "stickier" surface to the separated cells. The "slower" red cells, which have not migrated to the closed end 4 of the collection tube upon completion of centrifugation, adhere to or become imbedded in the layer 12 of the newtonian gel. Accordingly, with the present invention, fewer red cells are withdrawn with the mononuclear cells 22 when the mononuclear cells are removed.

FIG. 3 illustrates a more preferred form of the blood separation device of the present invention. As in the blood separation device of FIG. 1, the separation device illustrated by FIG. 3 includes a collection tube 2, with a closed bottom end 4 and an open top end 6, the tube defining a free space 14 to receive a sample of blood, and further includes a solution 16 of an anti-coagulant, a stabilizing reagent or combination of the two, a first layer 10 of a thixotropic gel-like substance, a second layer 12 of a newtonian gel-like substance positioned below the first layer 10, and a third layer 26 of a liquid density separation medium, positioned below the second layer 12 of newtonian gel and preferably at the closed end 4 of the collection tube.

The first layer 10 of thixotropic gel-like substance acts as a barrier, as in the previously described embodiment of FIG. 1, to maintain the second layer 12 of the newtonian gel-like substance and the third layer 26 of liquid density separation medium in the lower portion of the collection tube and separated from the blood sample or solution 16. The thixotropic gel-like substance of the first layer 10 has a specific gravity which is greater than that of the newtonian gel of the second layer 12 so that, upon centrifugation of the collection tube 2, it moves to a neutral position below the newtonian gel layer 12. However, it is also desired to form the thixotropic gel with a specific gravity which is less than that of the liquid density separation medium of the third layer 26, as will be explained in greater detail.

FIG. 4 shows the collection tube of FIG. 3 containing a blood sample after centrifugation. The red cells or erythrocytes 18, which are generally the heavier blood components, generally occupy the lowest portion of the collection tube at the closed end 4. The red cells 18 are followed by a layer of granulocytes 20, and above the granulocytes 20 is the layer 10 of thixotropic gel-like substance, which has moved from a position where it acted as a barrier to a position where it is out of the way of the actual separation between the mononuclear cells and the other blood components.

Atop the thixotropic gel layer 10 is the heavy phase portion 28 of the liquid density separation medium, which phase includes some residual red cells which have not migrated to the bottom of the collection tube. The heavy phase 28 of the liquid density separation medium is that portion which is substantially undiluted by the blood plasma.

The layer 12 of newtonian gel-like substance has moved upon centrifugation to above the layer 10 of thixotropic gel. The newtonian gel layer 12 has a "flypaper" effect in that it captures any residual red cells, which cells adhere to or imbed in this layer. Thus, the newtonian gel layer 12 keeps to a minimum the red cell contamination of the blood phase to be extracted.

Disposed directly above the newtonian gel layer 12 is the light phase 30 of the liquid density separation medium. The light phase 30 is generally believed to be caused by the red cells carrying the water component of the blood into the layer 26 of the density separation medium during centrifugation, which has the effect of diluting a portion of the liquid density medium such that its specific gravity is less than that of the newtonian gel. The red cells 18 and layer 10 of thixotropic gel, which are heavier than the light phase 30, help displace the light phase to a position above the newtonian gel layer 12. The mononuclear cells 22 reside directly above the light phase of the liquid density separation medium, and above the mononuclear cells 22 is the blood plasma 24 which, as described previously, may be pipetted off prior to extracting the mononuclear cells.

As also explained previously, the light phase 30 of the liquid density medium layer 26 is desired because it acts to buoy up the mononuclear cells 22, which tends to minimize the loss of those cells by their sticking to or imbedding in the newtonian gel layer 12. As a result, the cells are easily removed from the collection tube after separation with little loss of cells.

If it is desired to maintain the relative positions of the components of the blood separation device shown in FIG. 3 (i.e., the solution 16 of anti-coagulant and stabilizing reagent, and the layers of the thixotropic gel 10, newtonian gel 12 and liquid density separation medium 26) prior to centrifugation or during shipment, the embodiments illustrated by FIGS. 5 and 6 may be used.

The separation device illustrated by FIG. 5 is generally the same as that shown in FIG. 3 except that it further includes a porous foam member 32 which is inserted into the collection tube 2 and positioned at the bottom closed end 4 of the tube. The porous foam member 32 is used to absorb and retain the layer 26 of liquid density gradient medium or a substantial part thereof. The foam member 32 presents a mechanically stable barrier to the newtonian gel layer 12 and, in effect, holds the newtonian gel layer 12 and the liquid density separation medium layer 26 in position below the thixotropic gel layer 10 while not substantially reducing the blood capacity of the collection tube.

During centrifugation of the tube containing a blood sample, the red blood cells can enter the foam member 32 to displace the liquid density medium. If the volume of the foam member 32 is substantially equal to the density of the liquid gradient medium, then the reduction of the blood capacity of the tube will be negligible. The red blood cells will displace the density medium and generally occupy the lower portion of the collection tube 2, as they did in the previous embodiments. The foam member 32 may be formed from a number of materials, such as reticulated urethane foam.

Alternatively, and as illustrated by FIG. 6, a second layer 34 of a thixotropic gel-like substance may be positioned between the liquid density gradient medium layer 26 and the newtonian gel layer 12 in the device of FIG. 3 instead of using a porous foam member. The second layer 34 of thixotropic gel will maintain the relative positions of the newtonian gel layer 12 and the liquid density medium layer 26 in the collection tube, and will prevent the intermixing of the two when the tube is placed on its side.

In the embodiment illustrated by FIG. 3, because the newtonian gel layer 12 is not used as a barrier as it is in the prior art device described previously (because the thixotropic gel layer 10 functions as the barrier), but rather is primarily used to provide a sticky surface to capture any residual red cells which might have otherwise contaminated the mononuclear phase 22 after separation, the newtonian gel layer 12 may be of a substantially minimal amount, such as 0.5 ml for a standard 15 ml collection tube.

The thixotropic gel layer 10, which functions as a barrier between the blood sample or anti-coagulant and stabilizing reagent solution 16, and the newtonian gel layer 12 and the liquid density separation medium layer 26, should occupy a sufficient volume in the collection tube 2 to completely cover the cross-sectional area of the tube so to provide a proper barrier, even when the collection tube is stored for long durations on its side. A thixotropic gel layer in the amount of about 2.5 ml for a 10-15 ml standard centrifuge tube should be sufficient to form a barrier that will not slump.

One of the advantages of the present invention is that the blood separation device may be manufactured with all of its components, including the liquid density medium layer 26 and the solution 16 of a stabilizing reagent or anti-coagulant, in the same collection tube 2, which allows the tube to be used as a shipping container for the blood sample prior to centrifugation. The conventional blood separation device described previously did not have this capability, as the newtonian gel, when used as a barrier, would slump, allowing the anti-coagulant or stabilizing reagent to intermix with the liquid density medium and affect the medium's density and its cell separation properties.

One of the reasons that the collection tubes of blood separation devices are shipped on their sides from the physician, after the blood is drawn, to the clinical laboratory for processing is that as much of the blood sample as possible should be exposed to the stabilizing reagent or anti-coagulant in the collection tube. Such can be accomplished with the present invention, as the thixotropic gel layer 10, which acts as a barrier, will not slump in the collection tube 2 and thus will prevent the liquid density gradient material from intermixing with the blood sample or the anti-coagulant/stabilizing reagent in the tube.

Another advantage of the present invention is that the thixotropic gel-like substance of the first layer 10 may be either formed with hydrophobic or hydrophilic properties. This is because the thixotropic gel layer 10 is only used as a barrier and not as the separation medium and, upon centrifugation, will move to a neutral position where it will not impede the separation of the desired blood components. Accordingly, greater types of thixotropic gels may be used, including those which contain inorganic fillers that tend to absorb water and change performance characteristics when such are used as cell separation media.

Also, because the thixotropic gel layer 10 is used only as a barrier partition, the only required characteristic of the gel is it moves under centrifugation to a desired neutral position. Thus, the viscosity of the thixotropic gel is merely selected such that it stays within a range which allows movement of the gel layer 10 under centrifugation.

The only drawback to using a thixotropic gel which contains inorganic fillers that tend to absorb water is the possible whitish discoloration of the gel during long periods of storage as the gel absorbs water. Although this does not affect the barrier properties of the thixotropic gel layer 10, such whitish discoloration gives the appearance that the blood separation device is no longer useful. To overcome this problem, a coloring agent, such as titanium dioxide, may be added to the gel to minimize the change in appearance as the gel absorbs water.

The thixotropic gel layer 10 in the present invention not only acts as a barrier to maintain the relative position of the components of the separation device and to maintain the separation between the blood sample or solution 16 of anti-coagulant and stabilizing reagent, and the newtonian gel layer 12 and liquid density gradient material layer 26, but also, as described previously, acts as a displacement medium to move the light phase 30 of the liquid density medium layer 26 into its desired position above the newtonian gel layer 12.

Also, placement of the thixotropic gel layer 10 in the collection tube during manufacture is facilitated by the structure of the present invention. In a blood separation device which uses a liquid density separation medium and a thixotropic gel barrier atop the liquid density medium, such as described in co-pending application Ser. No. 653,178, filed Sept. 24, 1984, the thixotropic gel layer must be carefully positioned on the liquid density medium to ensure that the surface of the liquid density medium is not ruptured by the relatively "stiff" thixotropic gel substance. In the present invention, a newtonian gel layer 12 atop a liquid density medium layer 26 is less likely to rupture the liquid density medium, and the newtonian gel layer 12, which offers greater flow resistance than the liquid density medium, provides a stiffer surface which facilitates the placement of the thixotropic gel layer 10 thereon.

Because the thixotropic gel layer 10 is used only as a barrier and is unaffected by contact with aqueous solutions, both a stabilizing reagent and/or an anti-coagulant solution 16 and the liquid density medium layer 26 may be stored in contact with this barrier gel layer 10 without the two mixing. The use of a stabilizing reagent in a 1:1 dilution allows overnight shipment of the blood sample in the cell separation device to a reference laboratory without sample degradation, prior to separation using the same tube. The stabilizing reagent may include a culture medium, which tends to feed the cells and maintain their viability, if longer storage or shipment times are required.

The stabilizing reagent which may be used may typically be an isotonic or hypertonic solution, an ionic solution having a high molecular weight with organic molecules added, cell culture media such as RPMI 1640, and McCoy's medium. The stabilizing reagent is of a volume which is consistent with blood dilution ratios of from about 0.25:1 to about 3:1 of stabilizing reagent to blood.

As mentioned previously, the blood separation device of the present invention may be evacuated, and an anti-coagulant added to the stabilizing reagent, to allow the device to function as a direct draw blood collection tube.

As also mentioned previously, each of the embodiments of the present invention may include a closure 8 at the open end of the collection tube 2, which closure 8 allows sealing and sample entrance. The closure 8 may be in the form of a butyl rubber stopper with a septum suitable for penetration by a standard blood drawing needle.

The thixotropic gel used in the first layer 10 may be pre-saturated with water to limit its water absorption during storage with an aqueous solution. The thixotropic gel may be one of a variety of gels, including a silicone gel, a co-polyester resin based gel, polybutadiene and polybutene based gels, or for example, an a-olefin-dialkylmaleate co-polymer based gel.

The newtonian gel of the second layer 12 may also be selected from a variety of different organic resins which are hydrophobic, particularly resins which do not include inorganic fillers. Alternatively, the newtonian gel may be formed from a polyester resin which is essentially hydrophobic.

In the present invention, the separation medium, whether it be the liquid density separation medium layer 26 of the embodiment illustrated by FIG. 3 or the newtonian gel layer 12 of the embodiment illustrated by FIG. 1, is selected to have a specific gravity of between about 1.07 and about 1.09, but may have a specific gravity greater than 1.09.

The present invention provides a blood separation device which is shippable from the physician to the reference laboratory, as opposed to the conventional blood separation device described initially, but yet has all the advantages of the conventional blood separation device. Its manufacture is facilitated by the use of a newtonian gel layer 12 on which the thixotropic gel layer 10 is placed, and because the newtonian gel layer 12 no longer functions as a barrier and functions primarily to minimize red cell contamination, a much smaller volume of this material may be used.

The blood separation device containing a blood sample may be placed directly into a centrifuge and spun from about 1,000 to about 2,000 g's for about 10 to about 30 minutes to effect separation of the mononuclear cells or, more preferably, at about 1,500 g's for about 15 minutes.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of separating mononuclear cells from a sample of blood, which comprises the steps of:
    introducing a sample of blood into a blood separation device, the device including a collection tube, a first layer of a thixotropic gel-like substance contained in the collection tube, and a second layer of a newtonian gel-like substance contained in the collection tube and positioned below the first layer, the first layer of the thixotropic substance being positioned between the second layer of the newtonian substance and the blood sample received by the tube, prior to centrifuging the tube, and acting as a barrier between the second layer of the newtonian substance and the blood sample to prevent intermixing of the second layer and the blood sample, the thixotropic gel-like substance of the first layer having a specific gravity which is greater than that of the newtonian gel-like substance of the second layer, the newtonian gel-like substance acting as a density separation medium and being formed with a specific gravity such that it is adapted to assume a position in the collection tube between the mononuclear cells and the heavier components of a blood sample placed in the tube through centrifugation of the tube; and
    centrifuging the collection tube at a rate of about 1,000 to about 2,000 g's, the thixotropic gel layer moving to a position below the newtonian gel layer, and the newtonian gel layer assuming a position in the tube between the mononuclear cells and the heavier components of the blood sample.

2. A method as defined by claim 1, which further comprises the steps of removing plasma which has separated from the blood and adding a diluent to the mononuclear cells after the plasma has been removed to form a suspension disposed atop the layer of newtonian gel-like substance.

3. A method as defined by claim 2 which further comprises the step of removing the suspension from atop the layer of newtonian gel-like substance.

4. A method of separating mononuclear cells from a sample of blood, which comprises the steps of:
    introducing a sample of blood into a blood separation device, the device including a collection tube, a first layer of a thixotropic gel-like substance contained in the collection tube, a second layer of newtonian gel-like substance contained in the collection tube and positioned below the first layer, and a third layer of a liquid density separation medium contained in the tube and positioned below the second layer of the newtonian substance, the first layer of the thixotropic substance being positioned between the second layer of the newtonian substance and the blood sample received by the tube, prior to centrifuging the tube, and acting as a barrier between the blood sample and the second layer of the newtonian substance and the third layer of the liquid density separation medium to prevent intermixing of the second and third layers with the blood sample, the thixotropic gel-like substance of the first layer having a specific gravity which is greater than that of the newtonian gel-like substance of the second layer, the liquid density separation medium being formed with a specific gravity such that it is adapted to assume a position in the collection tube, upon centrifugation of the tube, between the mononuclear cells and the heavier components of the blood sample placed in the tube; and
    centrifuging the collection tube at a rate of about 1,000 to about 2,000 g's, at least a portion of the liquid density separation medium assuming a position in the tube between the mononuclear cells and the heavier components of the blood sample.

5. A method as defined by claim 4, which further comprises the steps of removing plasma which has separated from the blood and adding a diluent to the mononuclear cells after the plasma has been removed to form a suspension disposed atop the second layer of newtonian gel-like substance.

6. A method defined by claim 5, which further comprises the step of removing the suspension from atop the layer of newtonian gel-like substance.

7. Apparatus for separating mononuclear cells from blood, which comprises:
    a collection tube having a bottom closed end and an opposite top open end for receiving a blood sample, and being adapted to be centrifuged;
    a first layer of a thixotropic gel-like substance contained in the collection tube; and
    a second layer of a newtonian gel-like substance contained in the collection tube and positioned below the first layer;
    the collection tube being of sufficient size to define a free space above the first layer of thixotropic substance to receive the blood sample;
    the first layer of the thixotropic substance being positioned between the second layer of the newtonian substance and a blood sample received by the tube, prior to centrifuging the tube, and acting as a barrier between the second layer of the newtonian substance and the blood sample to prevent intermixing of the second layer and the blood sample;
    the thixotropic gel-like substance of the first layer having a specific gravity which is greater than that of the newtonian gel-like substance of the second layer, whereupon centrifugation of the tube, the first layer moves to a position below the second layer of newtonian substance;
    the second layer of the newtonian gel-like substance acting as a density separation medium, the newtonian gel-like substance thereof being formed with a specific gravity such that the second layer is adapted to assume a position in the collection tube, upon centrifugation of the tube, between the mononuclear cells and the heavier components of the blood sample placed in the tube.

8. An apparatus as defined by claim 7, wherein the newtonian gel of the second layer has a specific gravity of between about 1.07 and 1.09.

9. An apparatus as defined by claim 7, wherein the newtonian gel of the second layer is formed of an organic resin which is essentially hydrophobic.

10. An apparatus as defined by claim 7, wherein the newtonian gel of the second layer is formed of a polyester resin.

11. An apparatus as defined by claim 7, wherein the thixotropic gel of the first layer is selected from a group consisting of a silicone gel, a co-polyester resin based gel, a polybutadiene based gel, a polybutene based gel, and an a-olefin-dialkylmaleate co-polymer based gel.

12. An apparatus as defined by claim 7, wherein the thixotropic gel of the first layer is pre-saturated with water to limit water absorption.

13. An apparatus as defined by claim 7, wherein the thixotropic gel of the first layer includes a coloring agent to minimize appearance change caused by the absorption of water.

14. An apparatus as defined by claim 7, which further includes a stabilizing reagent contained in the collection tube, the stabilizing reagent being adapted to be mixed with a blood sample placed in the tube to minimize the aging of the blood cells of the blood sample and to thereby allow in vitro storage of blood sample in the collection tube.

15. An apparatus as defined by claim 14 the stabilizing reagent is selected from a group of stabilizing reagents consisting of an isotonic solution, a hypertonic solution, an ionic solution having high molecular weight organic molecules added, a cell culture media, and McCoy's medium.

16. An apparatus as defined by claim 7, which further includes closure means fitted onto the open top end of the collection tube.

17. An apparatus as defined by claim 7, wherein the free space defined by the collection tube is evacuated to allow the direct drawing of the blood sample.

18. Apparatus for separating mononuclear cells from blood, which comprises:
   a collection tube having a bottom closed end and an opposite top open end for receiving a blood sample, and being adapted to be centrifuged;
   a first layer of a thixotropic gel-like substance contained in the collection tube;
   a second layer of a newtonian gel-like substance contained in the collection tube and positioned below the first layer; and
   a third layer of a liquid density separation medium contained in the collection tube and positioned below the second layer of the newtonian substance and between the second layer and the bottom closed end of the tube;
   the collection tube being of sufficient size to define a free space above the first layer of thixotropic substance to receive the blood sample;
   the first layer of the thixotropic substance being positioned between the second layer of the newtonian substance and a blood sample received by the tube, prior to centrifuging the tube, and acting as a barrier between the blood sample and the second layer of the newtonian substance and the third layer of the liquid density separation medium to prevent intermixing of the second and third layers with the blood sample;
   the thixotropic gel-like substance of the first layer having a specific gravity which is greater than that of the newtonian gel-like substance of the second layer and less than that of the liquid density separation medium, whereupon centrifugation of the tube, the first layer moves to a position below the second layer of the newtonian substance
   the second layer of the newtonian gel-like substance having a specific gravity such that the second layer is adapted to assume a position in the collection tube above the first layer of thixotropic substance, upon centrifugation of the tube;
   the liquid density medium acting as a separation medium and being formed with a specific gravity such that the liquid density separation medium is adapted to assume a position in the collection tube, upon centrifugation of the tube, between the mononuclear cells and the heavier components of the blood sample placed in the tube.

19. An apparatus defined by claim 18, wherein the specific gravity of the liquid density separation medium of the third layer is between about 1.07 and about 1.09.

20. An apparatus as defined by claim 18, wherein the newtonian gel of the second layer is formed of an organic resin which is essentially hydrophobic.

21. An apparatus as defined by claim 18, wherein the newtonian gel of the second layer is formed of a polyester resin.

22. An apparatus as defined by claim 18, wherein the thixotropic gel of the first layer is selected from a group consisting of a silicone gel, a co-polyester resin based gel, a polybutadiene based gel, a polybutene based gel, and an a-olefin-dialkylmaleate co-polymer based gel.

23. An apparatus as defined by claim 18, wherein the thixotropic gel of the first layer is pre-saturated with water to limit water absorption.

24. An apparatus as defined by claim 18, wherein the thixotropic gel of the first layer includes a coloring agent to minimize appearance change caused by the absorption of water.

25. An apparatus as defined by claim 18, which further includes a stabilizing reagent contained in the collection tube, the stabilizing reagent being adapted to be mixed with a blood sample placed in the tube to minimize the aging of the blood cells of the blood sample and to thereby allow in vitro storage of the blood sample in the collection tube.

26. An apparatus as defined by claim 25, wherein the stabilizing reagent is selected from a group of stabilizing reagents consisting of an isotonic solution, a hypertonic solution, an ionic solution having high molecular weight organic molecules added, a cell culture media, and McCoy's medium.

27. An apparatus as defined by claim 18, which further includes closure means fitted onto the open top end of the collection tube.

28. An apparatus as defined by claim 18, wherein the free space defined by the collection tube is evacuated to allow the direct drawing of the blood sample.

29. An apparatus as defined by claim 18, which further comprises a porous foam member contained in the collection tube and positioned in proximity to the bottom closed end of the tube, the porous foam member being adapted to absorb the liquid density separation medium of the third layer contained in the tube.

30. An apparatus as defined by claim 29, where in the porous foam member is formed from a reticulated urethane foam.

* * * * *